United States Patent [19]
Pallos

[11] 4,071,556
[45] Jan. 31, 1978

[54] FORMAMIDINE INSECTICIDAL COMPOUNDS

[75] Inventor: Ferenc M. Pallos, Walnut Creek, Calif.

[73] Assignee: Stauffer Chemical Company, Westport, Conn.

[21] Appl. No.: 449,792

[22] Filed: Mar. 11, 1974

[51] Int. Cl.$^2$ .......................................... C07C 123/00
[52] U.S. Cl. .............................. 260/564 RF; 424/326
[58] Field of Search ................................. 260/564 RF

[56] References Cited
U.S. PATENT DOCUMENTS 3,557,128  1/1971  Pallos et al. .................. 260/546 RF

FOREIGN PATENT DOCUMENTS 797,442  9/1973  Belgium ........................ 260/564 RF
771,792  2/1972  Belgium ........................ 260/564 RF

*Primary Examiner*—Gerald A. Schwartz
*Attorney, Agent, or Firm*—Michael J. Bradley

[57] ABSTRACT

A composition of matter is described herein which has insecticidal and miticidal activity and methods of use. The composition may be defined by the following generic formula:

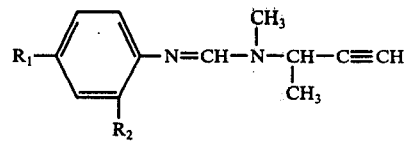

wherein $R_1$ and $R_2$ are independently methyl or halogen, preferably methyl or chlorine.

6 Claims, No Drawings

FORMAMIDINE INSECTICIDAL COMPOUNDS

BACKGROUND OF THE INVENTION

Among the many insecticidal and miticidal compounds available, various substituted formamidine compounds have shown such insecticidal and miticidal activity. Specific examples thereof and method of use are those described in U.S. Pat. Nos. 3,502,720 and 3,378,437.

BRIEF DESCRIPTION OF THE INVENTION

It has been discovered that certain substituted formamidine compounds are useful as insecticidal and miticidal compounds. These substituted formamidine compounds may be defined by the following generic formula:

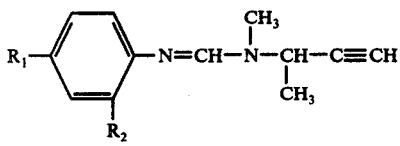

wherein $R_1$ and $R_2$ are independently methyl or halogen, preferably methyl or chlorine.

DETAILED DESCRIPTION OF THE INVENTION

In the practice of the present invention, the compounds of the present invention are manufactured by reacting the properly selected 2,4 disubstituted aniline with an alkyl orthoformate and then reacting the resulting alkylformimidate with 1-methyl-amino-1-methyl-propin-2 as shown by the following reaction scheme:

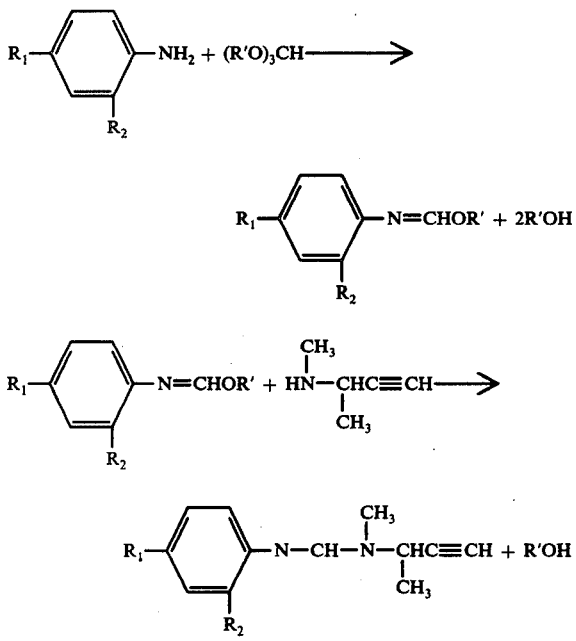

After the compounds of the present invention are formed, they can be applied to the habitat in an effective amount to control respective mites and insects.

The following examples illustrate the merits of the present invention:

EXAMPLE I

1-Methyl-1-(1'-methylpropin-2')-3-(2''-methyl-3''-chlorophenyl)-formamidine

Into a round-bottom flask fitted with a stirrer, was placed 4.0 g (0.02 mole) of O-Ethyl-N-(2-methyl-4-chlorophenyl)-formimidate, 10 ml $CH_2Cl_2$ and 6 ml of 1-methylamino-1-methyl-propin-2. The reacting solution was refluxed for 4 hours. After cooling the mixture was stripped by high vacuum. The reaction yielded 4.5 g of a solid product. Structure confirmation was by N.M.R.

Other compounds can be prepared in an analogous manner starting with the appropriate materials as outlined above. Following is a table of compounds representative of those embodied in the present invention. Compound numbers have been assigned to them and are used for identification throughout the balance of this specification.

TABLE I

| Compound Number | $R_1$ | $R_2$ |
|---|---|---|
| 1 | Cl | $CH_3$ |

Insecticidal activity of the above compounds were evaluated for efficacy on various insect species as follows:

I. Salt-marsh Caterpillar [*Estigmene acrea* (Drury)]

A. Leaf Dip Assay to Determine Efficacy Against First Instar Salt-marsh Caterpillar Larvae Kidney Bean leaves are dipped in a 50—50 acetone-water solution of the test chemical. When the leaves have dried, egg masses of the Salt-marsh Caterpillars are placed on the leaf surface. Mortality of the newly hatched larvae is determined after one week. Test concentrations range from 0.05% down to that at which approximately 50% of the larvae are dead.

B. Ovicidal Screening Procedure

Egg masses of the Salt-marsh Caterpillar are dipped in acetone solutions of the test chemicals and placed in petri dishes containing a portion of larval rearing medium. Efficacy is determined after seven days by observing the number of newly emerged larvae. Test concentrations range from 0.05% down to that at which approximately 50% of the eggs do not hatch.

II. Black Bean Aphid [*Aphis fabae* (Scop.)]

Nasturtium (*Tropaeolum* sp.) plants, approximately 2-3 inches tall, are transplanted into sandy loam soil in 3-inch clay pots and infested with 50-75 aphids of mixed ages. Twenty-four hours later they are sprayed, to the point of runoff, with aqueous suspensions of the toxicant. The suspensions are prepared by diluting aliquots of the toxicant, dissolved in an appropriate solvent, with water to which has been added 0.0002% of a conventional wetting agent such as polyoxy-ethylene sorbitan monolaurate ether of alkylated phenol blended with organic sulfonate. Test concentrations ranged from 0.05% to that at whch 50% mortality is obtained. Mortality is recorded after 48 hours and the LD-50 values are expressed as percent active ingredient in the aqueous suspensions.

III. Two-spotted Mite [*Tetranychus urtacae* (Koch)]

Pinto Beans (*Phaseolus* sp.) plants, approximately 2-3 inches tall, are transplanted into sandy loam soil in 3-inch clay pots and infested with 50-75 mites of mixed ages. Twenty-four hours later they are sprayed, to the point of runoff, with aqueous suspensions of the toxicant. The suspensions are prepared as in previously described tests (I and II). Test concentrations ranged from 0.05% to that at which 50% mortality is obtained. Mortality of adults, nymphs and eggs is recorded after 7 days and the LD-50 values are expressed as percent active ingredient in the aqueous suspensions.

IV. Systemic Tests

A. Salt-march Caterpillar:

Aliquots of toxicant dissolved in an appropriate solvent are diluted in water and placed in glass bottles. Concentrations of active ingredient range from 10 ppm to that at which 50% mortality is obtained. Kidney Beans (*Phaseolus vulgaris*), supported by cotton plugs, are inserted into the solution so that the roots and major portion of the stem are completely immersed. Masses of caterpillar eggs which are nearly ready to hatch are fastened to the bean leaves. One week later mortality of the newly hatched larvae is recorded. LD-50 values are expressed as ppm of toxicant in the aqueous suspensions.

B. Two-spotted Mite:

Preparation of the test solution and concentrations is the same as for the Salt-march Caterpillar test (IV-A). Pinto Bean (*Phaseolus* sp.) plants with expanded primary leaves are placed in the solution so that the roots and major portions of the stem are completely immersed. Immediately after, the leaves are infested with 75-100 mites of various ages. Mortality of adults, nymphs and eggs is recorded after one week, and LD-50 values are expressed as ppm of toxicant in the aqueous suspensions.

The results of the above test procedures indicate in Table II the effective concentration at which LD-50 control effect was achieved on the various species of insects.

TABLE II

| Compound Number | BA % | SMC | | | 2SM | | |
|---|---|---|---|---|---|---|---|
| | | Dip % | Leaf Ovicide % | SYS ppm | Pe % | Eggs % | SYS ppm |
| 1 | .05 | .0003 | .03 | .3 | .01 | .05 | 10 |

SMC = Salt-marsh Caterpillar
SYS = Systemic
2SM = Two-spotted Mite
BA = Bean Aphid
> = greater than
< = less than
Pe = Post-embryonic The compounds of this invention are generally embodied into a form suitable for convenient application. For example, the compounds can be embodied into pesticidal compositions which are provided in the form of emulsion, suspensions, solutions, dusts and aerosol sprays. In general, such compositions will contain, in addition to the active compound, the adjuvants which are normally found in pesticide preparations. In these compositions, the active compounds of this invention can be employed as a sole pesticide component or they can be used in a mixture with other compounds having similar utility. The pesticide compositions of this invention can contain as adjuvants organic solvents such as sesame oil; xylene solvents; heavy petroleum, etc.; water; emulsifying agents; surface active agents; talc, pyrophyllite; diatomite; gypsum; clays; propellents; such as dichlorodifluormethane, etc. If desired, however, the active compounds can be applied directly to feedstuffs, seeds, etc. upon which these pests feed. When applied in such a manner, it will be advantageous to use a compound which is not volatile. In connection with the activity of the presently disclosed pesticidal compounds, it should be fully understood that it is not necessary that they be active as such. The purposes of this invention will be fully served to the compound as rendered active by external influences, such as light or by some physiological action which occurs when the compound is ingested into the body of the pests.

The precise manner in which the pesticidal composition of this invention are used in any particular instance, will be readily apparent to a person skilled in the art. Generally, the active pesticide compound will be embodied in the form of a liquid composition. For example, an emulsion, suspension or aerosol spray. While the concentration of the active pesticide in the present compositions can vary within rather wide limits, ordinarily the pesticide compound will comprise not more than about 15.0% by weight of the pesticidal composition. Preferably, however, the pesticide compositions of this invention will be in the form of solutions or suspensions containing from about 0.1 to about 1.0% by weight of the active pesticide compound.

What is claimed is:

1. The compound having the formula:

$$R_1-\underset{R_2}{\underset{|}{\bigcirc}}-N=CH-\underset{|}{\overset{CH_3}{\underset{|}{N}}}-CHC\equiv CH$$
$$\phantom{R_1-\bigcirc-N=CH-N-}CH_3$$

wherein $R_1$ and $R_2$ are independently methyl or halogen.

2. A compound as set forth in claim 1 wherein $R_1$ and $R_2$ are independently methyl or chlorine.

3. A compound as set forth in claim 1 wherein $R_1$ is Cl and $R_2$ is $CH_3$.

4. A compound as set forth in claim 1 wherein $R_1$ is $CH_3$ and $R_2$ is Cl.

5. A compound as set forth in claim 1 wherein $R_1$ is $CH_3$ and $R_2$ is $CH_3$.

6. A compound as set forth in claim 1 wherein $R_1$ is Br and $R_2$ is $CH_3$.

* * * * *